United States Patent
Meyer et al.

(10) Patent No.: US 10,398,302 B2
(45) Date of Patent: Sep. 3, 2019

(54) ENHANCED VESSEL CHARACTERIZATION IN OPTICAL COHERENCE TOMOGRAOGPHY ANGIOGRAPHY

(71) Applicants: Carl Zeiss Meditec, Inc., Dublin, CA (US); CARL ZEISS MEDITEC AG, Jena (DE)

(72) Inventors: Scott A. Meyer, Livermore, CA (US); Utkarsh Sharma, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 160 days.

(21) Appl. No.: 15/303,819

(22) PCT Filed: Apr. 29, 2015

(86) PCT No.: PCT/EP2015/059378
§ 371 (c)(1),
(2) Date: Oct. 13, 2016

(87) PCT Pub. No.: WO2015/165989
PCT Pub. Date: Nov. 5, 2015

(65) Prior Publication Data
US 2017/0035286 A1 Feb. 9, 2017

Related U.S. Application Data

(60) Provisional application No. 61/987,669, filed on May 2, 2014.

(51) Int. Cl.
*A61B 3/14* (2006.01)
*A61B 3/00* (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
CPC ... A61B 3/0025; A61B 3/0033; A61B 3/0041; A61B 3/005; A61B 3/0058; A61B 3/022;
(Continued)

(56) References Cited

U.S. PATENT DOCUMENTS 6,549,801 B1 4/2003 Chen et al.
7,301,644 B2 11/2007 Knighton et al.
(Continued)

FOREIGN PATENT DOCUMENTS

JP 2009-165710 A 7/2009
WO 2010/030159 A2 3/2010
(Continued)

OTHER PUBLICATIONS

Al-Diri et al., "Automated Analysis of Retinal Vascular Network Connectivity", Computerized Medical Imaging and Graphics, vol. 34, 2010, pp. 462-470.
(Continued)

*Primary Examiner* — Mustak Choudhury
(74) *Attorney, Agent, or Firm* — Morrison & Foerster LLP

(57) ABSTRACT

Systems and methods to improve the visualization of vasculature in OCT angiography data are presented. In one embodiment, vessels having a particular orientation relative to one or more reference surfaces are highlighted. In another embodiment, the path of individual vessels can be analyzed to determine how many or what layers the vessels traverse. In another embodiment, regions which are typically not vascularized are analyzed for the presence of vessels. Techniques to minimize the impact of shadow artifacts are also presented and can be applied to any of the visualization approaches for further enhancement.

13 Claims, 6 Drawing Sheets

(51) Int. Cl.

| | |
|---|---|
| *A61B 3/10* | (2006.01) |
| *G06T 7/11* | (2017.01) |
| *G06T 7/187* | (2017.01) |
| *A61B 3/12* | (2006.01) |
| *G06T 7/00* | (2017.01) |

(52) U.S. Cl.
CPC .......... *A61B 3/1233* (2013.01); *G06T 7/0012* (2013.01); *G06T 7/11* (2017.01); *G06T 7/187* (2017.01); *G06T 2207/10101* (2013.01); *G06T 2207/30041* (2013.01)

(58) Field of Classification Search
CPC ........... A61B 3/063; A61B 3/14; A61B 3/102; A61B 3/1233; A61B 5/0066; A61B 5/0261; G06T 7/0012; G06T 7/11; G06T 7/73; G06T 7/187; G06T 2207/10101; G06T 2207/30041; G06T 2207/30101
USPC .................................. 351/206, 246; 382/107
See application file for complete search history.

(56) References Cited

U.S. PATENT DOCUMENTS

| | | | |
|---|---|---|---|
| 7,359,062 | B2 | 4/2008 | Chen et al. |
| 8,079,711 | B2 | 12/2011 | Stetson et al. |
| 8,090,164 | B2 | 1/2012 | Bullitt et al. |
| 8,332,016 | B2 | 12/2012 | Everett et al. |
| 8,433,393 | B2 | 4/2013 | Sharma et al. |
| 8,857,988 | B2 | 10/2014 | Sharma et al. |
| 2003/0208326 | A1 | 11/2003 | Chen et al. |
| 2004/0076262 | A1 | 4/2004 | Shao et al. |
| 2005/0171438 | A1 | 8/2005 | Chen et al. |
| 2007/0019846 | A1 | 1/2007 | Bullitt et al. |
| 2008/0025570 | A1* | 1/2008 | Fingler ................. A61B 3/102 382/107 |
| 2008/0100612 | A1 | 5/2008 | Dastmalchi et al. |
| 2008/0159604 | A1 | 7/2008 | Wang et al. |
| 2008/0291463 | A1 | 11/2008 | Milner et al. |
| 2009/0005693 | A1 | 1/2009 | Brauner et al. |
| 2009/0268162 | A1 | 10/2009 | Stetson et al. |
| 2009/0270738 | A1 | 10/2009 | Izatt et al. |
| 2010/0027857 | A1 | 2/2010 | Wang |
| 2010/0113900 | A1 | 5/2010 | Shakespeare et al. |
| 2010/0159497 | A1 | 6/2010 | Kimia et al. |
| 2010/0189334 | A1 | 7/2010 | Tomidokoro et al. |
| 2010/0240986 | A1 | 9/2010 | Stiles |
| 2010/0245770 | A1 | 9/2010 | Zhang et al. |
| 2011/0034803 | A1 | 2/2011 | Stetson |
| 2011/0063573 | A1 | 3/2011 | Meyer et al. |
| 2011/0103657 | A1 | 5/2011 | Kang et al. |
| 2011/0109881 | A1 | 5/2011 | Munger et al. |
| 2011/0164791 | A1 | 7/2011 | Bajraszewski et al. |
| 2011/0169978 | A1 | 7/2011 | Lasser et al. |
| 2011/0243408 | A1 | 10/2011 | Takama |
| 2012/0035454 | A1 | 2/2012 | Tearney et al. |
| 2012/0053904 | A1 | 3/2012 | Yuasa et al. |
| 2012/0063665 | A1 | 3/2012 | Wang et al. |
| 2012/0075638 | A1 | 3/2012 | Rollins et al. |
| 2012/0120408 | A1 | 5/2012 | Yasuno et al. |
| 2012/0140171 | A1 | 6/2012 | Hirose et al. |
| 2012/0150048 | A1 | 6/2012 | Kang et al. |
| 2012/0218516 | A1 | 8/2012 | Imamura et al. |
| 2012/0218517 | A1 | 8/2012 | Imamura |
| 2012/0249956 | A1 | 10/2012 | Stetson |
| 2012/0274745 | A1 | 11/2012 | Russell |
| 2012/0274897 | A1 | 11/2012 | Narasimha-Iyer et al. |
| 2012/0277570 | A1 | 11/2012 | Todor et al. |
| 2012/0277579 | A1 | 11/2012 | Sharma et al. |
| 2012/0307014 | A1 | 12/2012 | Wang |
| 2013/0018254 | A1 | 1/2013 | Drucker |
| 2013/0094720 | A1 | 4/2013 | Stetson |
| 2013/0094725 | A1 | 4/2013 | Gulsun et al. |
| 2013/0215235 | A1 | 8/2013 | Russell |
| 2013/0301008 | A1 | 11/2013 | Srivastava et al. |
| 2014/0028974 | A1 | 1/2014 | Tumlinson |
| 2014/0049632 | A1 | 2/2014 | Hemmer |
| 2014/0073915 | A1 | 3/2014 | Lee et al. |
| 2014/0293222 | A1 | 10/2014 | Coelho et al. |
| 2015/0062590 | A1 | 3/2015 | Bagherinia |

FOREIGN PATENT DOCUMENTS

| | | | | |
|---|---|---|---|---|
| WO | | 2010/129494 | A2 | 11/2010 |
| WO | | 2010/131944 | A2 | 11/2010 |
| WO | | 2010/138645 | A2 | 12/2010 |
| WO | WO | 2010/138645 | A2 * 12/2010 | ........... A61B 5/0073 |
| WO | | 2010/129494 | A3 | 2/2011 |
| WO | | 2011/097631 | A2 | 8/2011 |
| WO | | 2011/097631 | A3 | 11/2011 |

OTHER PUBLICATIONS

An et al., "In vivo Volumetric Imaging of Vascular Perfusion within Human Retina and Choroids with Optical Micro-Angiography", Optics Express, vol. 16, No. 15, 2008, pp. 11438-11452.

An et al., "Optical Microangiography Provides Correlation between Microstructure and Microvasculature of Optic Nerve Head in Human Subjects", Journal of Biomedical Optics, vol. 17, No. 11, Nov. 2012, pp. 116018-1-116018-6.

An et al., "Ultrahigh Sensitive Optical Microangiography for in vivo Imaging of Microcirculations within Human Skin Tissue Beds", Optics Express, vol. 18, No. 8, 2010, pp. 8220-8228.

Avakian et al., "Fractal Analysis of Region-based Vascular Change in the Normal and Non-Proliferative Diabetic Retina", Current Eye Research, vol. 24, No. 4, 2002, pp. 274-280.

Debuc, Delia C., "A Review of Algorithms for Segmentation of Retinal Image Data Using Optical Coherence Tomography", Image Segmentation InTech, Chapter 2, 2011, pp. 15-54.

Enfield et al., "In Vivo Imaging of the Microcirculation of the Volar Forearm using Correlation Mapping Optical Coherence Tomography (cmOCT)", Biomedical Optics Express, vol. 2, No. 5, May 1, 2011, pp. 1184-1193.

Final Office Action received for U.S. Appl. No. 13/781,375 dated Mar. 3, 2015, 14 pages.

Fingler et al., "Mobility and Transverse Flow Visualization using Phase Variance Contrast with Spectral Domain Optical Coherence Tomography", Optics Express, vol. 15, No. 20, Sep. 18, 2007, pp. 12636-12653.

Fingler et al., "Volumetric Microvascular Imaging of Human Retina using Optical Coherence Tomography with a Novel Motion Contrast Technique", Optics Express, vol. 17, No. 24, Nov. 19, 2009, pp. 22190-22200.

Frangi et al., "Multiscale Vessel Enhancement Filtering", Lecture Notes in Computer Science, vol. 1496, 1998, 8 pages.

Ganesan et al., "Development of an Image-Based Network Model of Retinal Vasculature", Annals of Biomedical Engineering, vol. 38, No. 4, Apr. 2010, pp. 1566-1585.

Herfkens, Robert, "Computational Visualization of 4D Cardiac Flow", Available at <http://www.nvidia.com/object/quadro-fermi-video-view04.html>, 2010, 1 page.

Herman, Kevin C., "Crossing the Challenging Aortic Bifurcation", Endovascular Today, Jan. 2012, pp. 45-49.

Hillmann et al., "Holoscopy-Holographic Optical Coherence Tomography", Optics Letters, vol. 36, No. 13, Jul. 1, 2011, pp. 2390-2392.

International Preliminary Report on Patentability received for PCT Patent Application No. PCT/EP2013/059560, dated Nov. 20, 2014, 8 pages.

International Search Report and Written Opinion received for PCT Patent Application No. PCT/EP2013/059560, dated Aug. 27, 2013, 6 pages.

International Search Report received for PCT Patent Application No. PCT/EP2015/059378, dated Dec. 14, 2015, 6 pages.

Ishikawa et al., "Macular Segmentation with Optical Coherence Tomography", Investigative Ophthalmology & Visual Science, vol. 46, No. 6, Jun. 2005, pp. 2012-2017.

(56) References Cited

OTHER PUBLICATIONS

Jia et al., "Optical Coherence Tomography Angiography of Optic Disc Perfusion in Glaucoma", Ophthalmology, vol. 121, No. 7, Jul. 2014, pp. 1322-1332.
Jia et al., "Quantitative OCT Angiography of Optic Nerve Head Blood Flow", Biomedical Optics Express, vol. 3, No. 12, 2012, pp. 3127-3137.
Jia et al., "Split-Spectrum Amplitude-Decorrelation Angiography with Optical Coherence Tomography", Optics Express, vol. 20, No. 4, Feb. 9, 2012, pp. 4710-4725.
John et al., "Dimensions of the Foveal Avascular Zone using the Heidelberg Retinal Angiogram-2 in Normal Eyes", Indian Journal of Ophthalmology, vol. 59, No. 1, 2011, 6 pages.
Joshi, Vinayak Shivkumar, "Analysis of Retinal Vessel Networks Using Quantitative Descriptors of Vascular Morphology", University of Iowa, IOWA Research Online, Theses and Dissertations, 2012, 182 pages.
Kim et al., "In vivo Volumetric Imaging of Human Retinal Circulation with Phase-Variance Optical Coherence Tomography", Biomedical Optics Express, vol. 2, No. 6, 2011, pp. 1504-1513.
Kim et al., "Noninvasive Imaging of the Foveal Avascular Zone with High-Speed, Phase-Variance Optical Coherence Tomography", Investigative Ophthalmology & Visual Science, vol. 53, No. 1, Jan. 2012, pp. 85-92.
Kim, M. K., "Tomographic Three-Dimensional Imaging of a Biological Specimen Using Wavelength-Scanning Digital Interference Holography", Optics Express, 7, No. 9, Oct. 23, 2000, pp. 305-310.
Kirbas et al., "A Review of Vessel Extraction Techniques and Algorithms", Jan. 2003, 52 pages.
Kirkpatrick et al., "OCT-Based Elastography for Large and Small Deformations", Optics Express, vol. 14, No. 24, Nov. 13, 2006, pp. 11585-11597.
Leitgeb et al., "Real-Time Assessment of Retinal Blood Flow with Ultrafast Acquisition by Color Doppler Fourier Domian Optical Coherence Tomography", Optics Express, vol. 11, No. 23, 2003, pp. 3116-3121.
Leitgeb et al., "Ultrahigh Resolution Fourier Domain Optical Coherence Tomography", Optics Express, vol. 12, No. 10, May 17, 2004, pp. 2156-2165.
Liu et al., "Intensity-Based Modified Doppler Variance Algorithm: Application to Phase Instable and Phase Stable Optical Coherence Tomography Systems", Optics Express, vol. 19, No. 12, Jun. 6, 2011, pp. 11429-11440.
Lujan et al., "Revealing Henle's Fiber Layer Using Spectral Domain Optical Coherence Tomography", Investigative Ophthalmology & Visual Science, vol. 52, No. 3, Mar. 2011, pp. 1486-1492.
Makita et al., "Comprehensive in vivo Micro-Vascular Imaging of the Human Eye by Dual-Beam-Scan Doppler Optical Coherence Angiography", Optics Express, vol. 19, No. 2, Jan. 17, 2011, pp. 1271-1283.
Makita et al., "Optical Coherence Angiography for the Eye", SPIE, Jun. 10, 2009, pp. 1-3.n.
Makita et al., "Optical Coherence Angiography", Optics Express, vol. 14, No. 17, Aug. 21, 2006, pp. 7821-7840.
Mariampillai et al., "Optimized Speckle Variance OCT Imaging of Microvasculature", Optics Express, vol. 35, No. 8, Apr. 15, 2010, pp. 1257-1259.
Mariampillai et al., "Speckle Variance Detection of Microvasculature Using Swept-Source Optical Coherence Tomography", Optics Letters, vol. 33, No. 13, Jul. 1, 2008, pp. 1530-1532.
Nam et al., "Complex Differential Variance Algorithm for Optical Coherence Tomography Angiography", Biomedical Optics Express, vol. 5, No. 11, Nov. 1, 2014, pp. 3822-3832.
Non-Final Office Action received for U.S. Appl. No. 13/543,373, dated Sep. 25, 2012, 9 pages.
Non-Final Office Action received for U.S. Appl. No. 13/781,375, dated Jun. 19, 2015, 17 pages.
Non-Final Office Action received for U.S. Appl. No. 13/781,375, dated Jun. 20, 2014, 18 pages.
Non-Final Office Action received for U.S. Appl. No. 13/854,623, dated Jan. 23, 2015, 8 pages.
Notice of Allowance received for U.S. Appl. No. 13/543,373, dated Jan. 2, 2013, 5 pages.
Notice of Allowance received for U.S. Appl. No. 13/854,623, dated Apr. 20, 2015, 9 pages.
Pajak, R. , "Use of Two-Dimensional Matched Filters for Estimating a Length of Blood Vessels Newly Created in Angiogenesis Process", Opto-Electronics Review, vol. 11, No. 3, 2003, pp. 237-242.
Popovic et al., "Noninvasive Imaging of Human Foveal Capillary Network Using Dual-Conjugate Adaptive Optics", Investigative Ophthalmology & Visual Science, vol. 52, No. 5, Apr. 2011, pp. 2649-2655.
Ralston et al., "Interferometric Synthetic Aperture Microscopy", Nature Physics, vol. 3, Feb. 2007, pp. 129-134.
Ramezani et al., "Agreement Between Clinical Estimation and a New Quantitative Analysis by Photoshop Software in Fundus and Angiographic Image Variables", Int. Ophthalmol, vol. 29, Sep. 19, 2008, pp. 439-449.
Reif et al., "Quantifying Optical Microangiography Images Obtained from a Spectral Domain Optical Coherence Tomography System", Hindawi Publishing Corporation, International Journal of Biomedical Imaging, vol. 2012, Article ID 509783, pp. 1-11.
Riva et al., "Laser Doppler measurements of blood flow in capillary tubes and retinal arteries", Investigative Ophthalmology, vol. 11, Nov. 1972, pp. 936-944.
Rollins et al., "Real-time in vivo color Doppler optical coherence tomography", Journal of Biomedical Optics, vol. 7, No. 1, Jan. 2002, pp. 123-129.
Salem et al., "Segmentation of Retinal Blood Vessels Based on Analysis of the Hessian Matrix and Clustering Algorithm", 15th European Signal Processing Conference, (EUSIPCO 2007), Sep. 3-7, 2007, pp. 428-432.
Schmidt-Erfurth et al., "Three-Dimensional Topographic Angiography in Chorioretinal Vascular Disease", Investigative Ophthalmology & Visual Science, 42, No. 10, Sep. 2001, pp. 2386-2394.
Schmitt Joseph M., "OCT Elastography: Imaging Microscopic Deformation and Strain of Tissue", Optics Express, vol. 3, No. 6, Sep. 14, 1998, pp. 199-211.
Schmoll et al., "Imaging of the Parafoveal Capillary Network and its Integrity Analysis using Fractal Dimension", Biomedical Optics Express, vol. 2, No. 5, 2011, pp. 1159-1168.
Spaide et al., "Fundus Autofluorescence and Central Serous Chorioretinopathy", American Academy of Ophthalmology, vol. 112, No. 5, May 2005, pp. 825-833.
Thorell et al., "Swept-Source OCT Angiography of Macular Telangiectasia Type 2", Ophthalmic Surg Lasers Imaging Retina, vol. 45, No. 5, Oct. 2014, pp. 369-380.
Vickerman et al., "VESGEN 2D: Automated, User-Interactive Software for Vascular Quantification and Mapping of Angiogenic and Lymphangiogenic Trees and Networks", Anat Rec (Hoboken), vol. 292, No. 3, Mar. 2009, 22 pages.
Wang, et al., "Depth-Resolved Imaging of capillary Networks in Retina and Choroid using Ultrahigh Sensitive Optical Microangiography", Optics Express, vol. 35, No. 9, May 1, 2010, pp. 1467-1469.
Wang et al., "Frequency Domain Phase-Resolved Optical Doppler and Doppler Variance Tomography", Optics Communications, vol. 242, 2004, pp. 345-350.
Wang et al., "Imaging Retinal Capillaries Using Ultrahigh-Resolution Optical Coherence Tomography and Adaptive Optics", Investigative Ophthalmology & Visual Science, vol. 52, No. 9, Aug. 2011, pp. 6292-6299.
Wang et al., "Three Dimensional Optical Angiography", Optics Express, vol. 15, No. 7, Apr. 2, 2007, pp. 4083-4097.
White et al., "In vivo Dynamic Human Retinal Blood Flow Imaging using Ultra-High-Speed Spectral Domain Optical Doppler Tomography", Optics Express, vol. 11, No. 25, 2003, pp. 3490-3497.
Yazdanfar et al., "Imaging and Velocimetry of the Human Retinal Circulation with Color Doppler Optical Coherence Tomography", Optics Express, vol. 25, No. 19, Oct. 1, 2000, pp. 1448-1450.

(56) References Cited

OTHER PUBLICATIONS

Zhang et al., "Minimizing Projection Artifacts for Accurate Presentation of Choroidal Neovascularization in OCT Micro-Angiography", Biomedical Optics Express, vol. 6, No. 10, 2015, pp. 4130-4143.

Zhao et al., "Doppler Standard Deviation Imaging for Clinical Monitoring of in vivo Human Skin Blood Flow", Optics Letters, vol. 25, No. 18, Sep. 15, 2000, pp. 1358-1360.

Zheng et al., "Automated Segmentation of Foveal Avascular Zone in Fundus Fluorescein Angiography", Investigative Ophthalmology & Visual Science, vol. 51, No. 7, Jul. 2010, pp. 3653-3659.

Zotter et al., "Visualization of Microvasculature by Dual-Beam Phase-Resolved Doppler Optical Coherence Tomography", Optics Express, vol. 19, No. 2, 2011, pp. 1217-1227.

\* cited by examiner

ENHANCED VESSEL CHARACTERIZATION IN OPTICAL COHERENCE TOMOGRAOGPHY ANGIOGRAPHY

PRIORITY

This application is a National Phase application under 35 U.S.C. § 371 of International Application No. PCT/EP2015/059378, filed Apr. 29, 2015, which claims priority to U.S. Provisional Application Ser. No. 61/987,669, filed May 2, 2014, the contents of each of which are hereby incorporated by reference.

TECHNICAL FIELD

The present invention relates to medical imaging, and in particular to analysis and visualization methods for vasculature image data acquired through interferometric imaging techniques such as optical coherence tomography.

BACKGROUND

Optical coherence tomography (OCT) is a noninvasive, noncontact imaging modality that uses coherence gating to obtain high-resolution cross-sectional images of tissue microstructure. Several implementations of OCT have been developed. In Frequency domain or Fourier domain OCT (FD-OCT), the interferometric signal between light from a reference and the back-scattered light from a sample point is recorded in the frequency domain either by using a dispersive spectrometer in the detection arm in the case of spectral-domain OCT (SD-OCT) or rapidly tuning a swept laser source in the case of swept-source OCT (SS-OCT). After a wavelength calibration, a one-dimensional Fourier transform is taken to obtain an A-line spatial intensity distribution of the object scattering in the depth dimension.

There are several intensity and/or phase-resolved data based OCT techniques, collectively named OCT Angiography, that have been utilized to map the retinal vasculature or identify regions with flow in the tissue (see for example An et al. "Optical microangiography provides correlation between microstructure and microvasculature of optic nerve head in human subjects," J. Biomed. Opt. 17, 116018, 2012, Zhao et al., "Doppler standard deviation imaging for clinical monitoring of in vivo human skin blood flow," Optics Letters 25, 1358-1360, 2000, Fingler et al. "Mobility and transverse flow visualization using phase variance contrast with spectral domain optical coherence tomography" Optics Express. Vol. 15, No. 20. pp 12637-12653, 2007, Makita et al., "Optical Coherence Angiography," Optics Express, 14(17), 7821-7840, 2006, Mariampillai et al., "Optimized speckle variance OCT imaging of microvasculature," Optics Letters 35, 1257-1259, 2010, and Wang et al., "Frequency domain phase-resolved optical Doppler and Doppler variance tomography" Optics Communications 242 345-350, 2004 hereby incorporated by reference). OCT Angiography, a non-invasive technique to visualize detailed vasculature or regions of flow, could provide doctors useful clinical information for diagnosis and management of eye diseases.

Conventional techniques to visualize retinal vasculature are invasive in nature, and use pharmacological techniques to modify contrast in the imaged retina. Contemporary clinical practice involves injection of a fluorescent dye (such as fluorescein (FA) or indocyanine green (ICG)) into the systemic circulation, and the eye is then scanned to generate an image, which selectively shows the path of the dye through the vascular network. In typical commercial fundus imaging systems, no information of the depth structure of the vasculature is captured by this method. In contrast, vascular images generated by examining the OCT signal are non-invasive, and provide comparable fidelity in capturing the existing vascular network with blood flow contrast along with its depth encoding. Retinal Function Imager (Optical Imaging Ltd.) used an approach of obtaining fast sequential fundus images by using stroboscopic illumination and generating vasculature maps by tracking motion of erythrocytes or blood cells. While this approach was non-invasive in nature, it lacked the depth information. Confocal laser scanning topography has been used to generate 3D profile of surface of vascular structures in the eye (Schmidt-Erfurth et al., "Three-Dimensional Topographic Angiography in Chorioretinal Vascular Disease," IOVS, 42 (10), 2386-2394, 2001). However, this approach cannot provide high axial resolution as OCT and is highly susceptible to artifacts caused by eye motion.

Diagnostically, changes to both the vascular and the typically avascular retina are important indicators of developing retinal pathologies. Although visualization of the vascular structure helps in boosting the diagnostic efficacy of this imaging technique, it can be further leveraged by augmenting the visualization with some salient quantifications and metrics derived from the identified vascular and avascular sections of the retina. A primary quantity of interest is the global or structure-specific retinal blood flow kinetics, which can be challenging to quantify because of low flow velocities relative to the temporal resolution of the technique, and the almost perpendicular orientation of the capillaries with respect to the probing beam. In addition to visualization, derived quantifiers from the angiography data which serve to aid in differentiating vascular networks in healthy and diseased eyes are also desirable.

Several research groups have explored quantitative methods for angiography data to construct meaningful numerical indicators of vascular pathology from traditional and OCT angiography data. (see for example Avakian, et al., "Fractal analysis of region-based vascular change in the normal and non-proliferative diabetic retina," Curr. Eye Res. 24, 274-280, 2002, Schmoll et al. "Imaging of the parafoveal capillary network and its integrity analysis using fractal dimension" Biomed. Opt. Express 2, 1159-1168, 2011, Jia et al., "Quantitative OCT angiography of optic nerve head blood flow," Biomed. Opt. Express 3, 3127-3137, 2012, An et al., "Optical microangiography provides correlation between microstructure and microvasculature of optic nerve head in human subjects," J. Biomed. Opt. 17, 116018, 2012 and Jia et al. "OCT Angiography of Optic Disc Perfusion in Glaucoma" Ophthalmology, 121 (7), 1322-1332, 2014).

One piece of important anatomical information that is captured by OCT angiography is the depth information, or the spatial distribution of the vessels in the retinal tissue. To visualize the complex capillary networks and to make use of the additional depth information gained by OCT angiography compared to traditional angiography methods such as FA, OCT angiography data is often displayed as 2D projections with the color encoded depth information (see Kim et al. "In vivo volumetric imaging of human retinal circulation with phase variance OCT," Biomedical Optics Express, 2(6), 1504-1513 2011). Such 2D projections at least allow distinguishing capillary layers of different depths. They however lack the 3D impression and also do not provide easily accessible information of which larger retinal vessels feed and drain different capillary network regions. Retinal vessel connectivity measures are also known for fundus photography (see for example Al-Diri et al. "Automated analysis of retinal vascular network connectivity," Computerized Medical Imaging and Graphics, 34, 462-470, 2010 and Ganesan et al. "Development of an Image-Based Network Model of Retinal Vasculature," Annals of Biomedical Engineering 38(4) 1566-1585, 2010).

Retinal vessels are not always constrained to the layers containing the capillary beds, and there is a need to facilitate the visualization and identification of such vessels. There are several ocular diseases including, but not limited to, macular telangiectasia, choroidal neovascularization (CNV), neovascularization elsewhere (NVE) etc., where there is growth of new vasculature that may abruptly dive through the retinal layers or even cause disruptions in it. In diseases such as Retinal Angiomatous Proliferation (RAP), new vessels grow which connect the retinal vasculature with the choroidal vasculature, with increasing neovascularization at more advanced disease stages. The resulting intra-retinal neovascularization and subretinal neovascularization are important features to identify in the diagnosis and staging of disease. For instance, appropriate clinical treatments and expected outcomes are different for choroidal neovascularization than for so-called masquerades such as RAP. Historically, angiography (FA and ICG) has been used to identify these cases. There is a need for more convenient detection of this neovascularization without the use of invasive imaging dye-based techniques like angiography. Depth resolved imaging by optical coherence tomography can be used for this purpose. For instance, vessels linking retinal and choroidal vasculature can be detected in B-scan intensity images. However, detailed inspection of volumetric data sets as a series of B-scans is impractical in a routine clinical practice. Srivastava et al. recently suggested several ways to improve the display of depth information (US Patent Publication No. 2013/0301008 hereby incorporated by reference). Here we propose further and alternative ways to enhance visualization and improve the clinical value of OCT angiography data.

SUMMARY

Aspects of the present application are directed to improved visualization of vasculature in OCT angiography data, focusing in particular on ways to enhance visualization of OCT angiography data to provide potentially meaningful information to the clinician in an efficient manner. In one embodiment, vessels having a particular orientation relative to one or more reference surfaces are highlighted. For this, the orientation of a vessel relative to a surface of interest such as a retinal layer boundary can be used to derive a metric to identify vessels having a particular orientation relative to the surface, for instance extending beyond the surface. In another embodiment, the path of individual vessels can be analyzed to determine how many or what layers the vessels traverse. In another embodiment, regions which are typically not vascularized are analyzed for the presence of vessels. Techniques to minimize the impact of shadow artifacts are also presented and can be applied to any of the visualization approaches for further enhancement.

DETAILED DESCRIPTION

Figure 1:
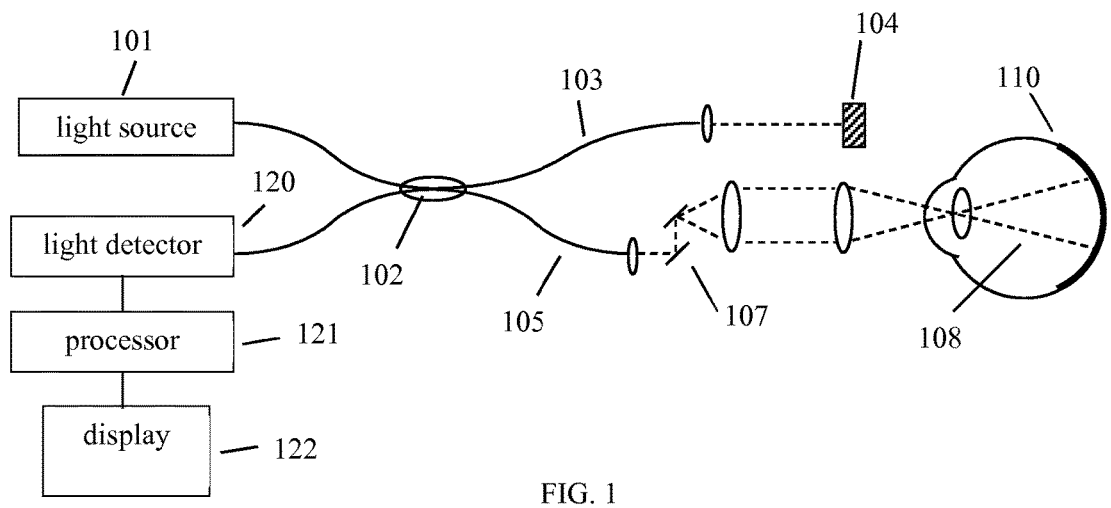
FIG. 1 is a diagram of a generalized FD-OCT system that could be used to collect OCT angiography data.

A diagram of a generalized FD-OCT system is shown in FIG. 1. Light from source 101 is routed, typically by optical fiber 105, to illuminate the sample 110, a typical sample being tissues in the human eye. The source 101 could be a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over a range of transverse locations on the sample to cover a region or regions to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector is supplied to a processor 121 where the interference signals generated in the detector are transformed and processed as described in further detail below. The results can be stored in the processor 121 or displayed on display 122. The processing and storing functions may be localized within the OCT instrument in one or more processors or functions may be performed on an external processing unit to which the collected data is transferred. This unit could be dedicated to data processing or perform other tasks which are quite general and not dedicated to the OCT device. One or more of the processors can be of the parallel processing type such as GPUs, FPGAs, or multi-core processors.

Figure 2:
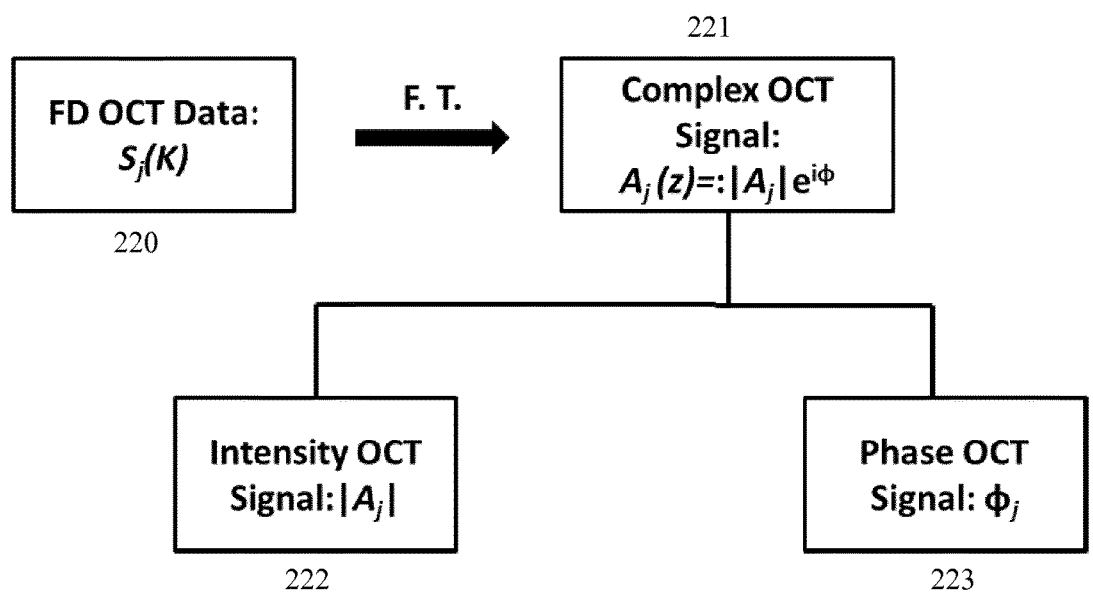
FIG. 2 illustrates how FD-OCT data is processed to yield phase and intensity signals.

As is illustrated schematically in FIG. 2, in Fourier Domain optical coherence tomography (FD-OCT), each measurement is the real-valued spectral interferogram ($S_j(k)$) (220). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$ (221). The absolute value of this complex OCT signal, $|A_j|$ (222), reveals the profile of scattering intensities at different path lengths, and therefore scattering as a function of depth (z-direction) in the sample (see for example Leitgeb et al. "Ultrahigh resolution Fourier domain optical coherence tomography," *Optics Express* 12(10) 2156 2004). Similarly, the phase, $\varphi_j$ (223) can also be extracted from the complex valued OCT signal. It should be noted that the application of the methods described herein could be applied to data acquired via many OCT variants including multi-beam OCT, and other parallel OCT imaging configurations. The related fields of optical diffraction tomography, holoscopy, digital interference holography, holographic OCT, and interferometric synthetic aperture microscopy are also capable of producing data suitable for angiographic analysis as described herein. (see for example US Patent Publication No. 2014/0028974, Hillman et al. "Holoscopy-holographic optical coherence tomography" Optics Letters, 36(13), 2390-2392, 2011; Kim, M.-K, "Tomographic three-dimensional imaging of a biological specimen using wavelength-scanning digital interference holography" Optics Express, 7(9), 305-310, 2000, and Ralston et al., "Interferometric synthetic aperture microscopy" Nature Physics, 3(2), 129-134, 2007)

Figure 3:
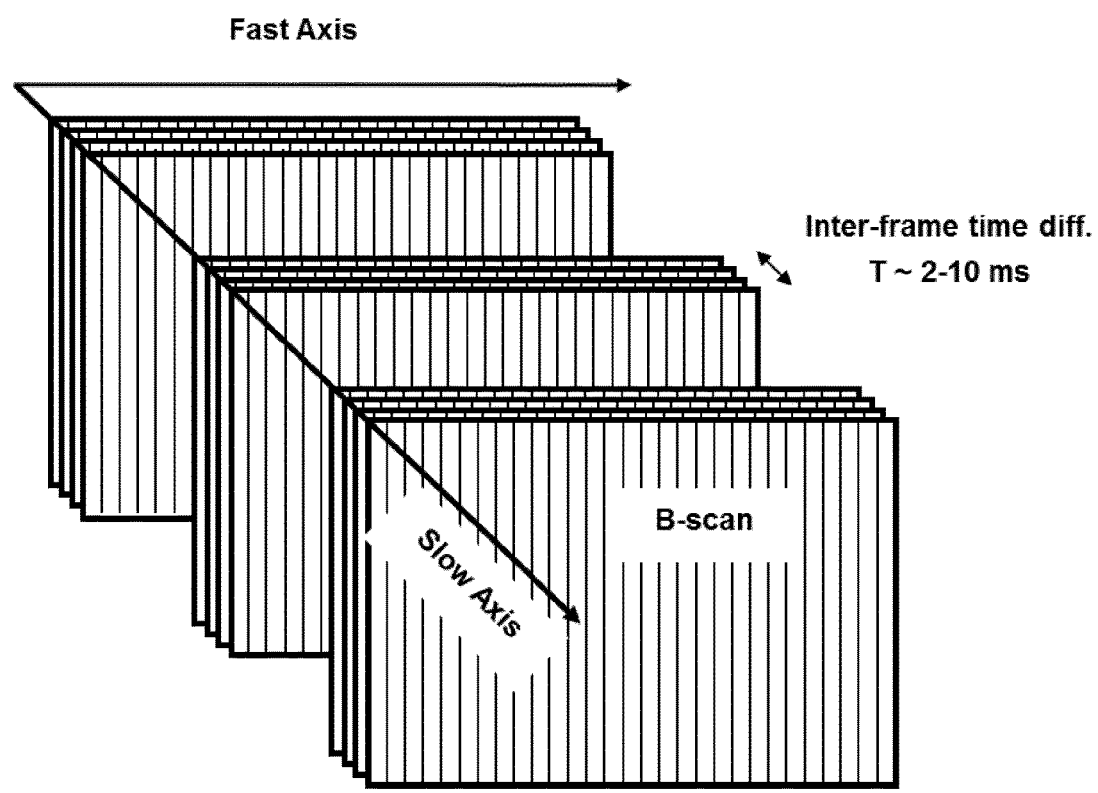
FIG. 3 illustrates a scan pattern for collecting OCT data for motion contrast processing.

The profile of scattering as a function of depth is called an axial scan (A-scan). A set of A-scans measured at neighboring locations in the sample produces a cross-sectional image (tomogram or B-scan) of the sample. A set of B-scans collected at the same or closely spaced locations on the tissue can be used in motion contrast techniques. One such scanning protocol commonly referred to as MB scanning is shown in FIG. 3. Here a series of A-scans are collected along an axis (labeled Fast axis) to generate a B-scan. The scanning is repeated at the same or densely spaced locations over time (represented by the slow axis) referred to herein as cluster scans. An inter-frame comparison refers to comparing consecutive B-scans from approximately the same location. The inter-frame time difference between consecutive B-scans depends on the system speed (A-line rate), number of A-scans in a single B-scan and the time it takes to return to the start position (fly-back times) but is typically on the order of 2-20 ms. Another scanning protocol that may be more suitable for higher speed OCT systems is to obtain a set of B-scans that are placed at different spatial locations and then to repeat the same set of B-scans at least once. Effectively, one would be repeating sub-volume or volume OCT acquisitions while making sure that the same region is scanned at least twice. In another scanning protocol, multiple inter-frame time differences can be achieved by having at least two consecutive B-scans at a given location and then re-scanning that location after a time delay of at least one B-scan. For example, one such implementation could be: BL1, BL1, BL2, BL2, BL1, BL3, BL3, BL2, BL4, BL4, BL3, and so forth. Here BL1 implies a B-scan at location 1, BL2 implies a B-scan at location 2 and so forth. The advantage of such scanning protocol is that one could have variable interframe time differences and it can allow improved detection sensitivity for different flow velocity ranges.

The complex valued OCT signal for the scan-pattern illustrated in FIG. 3 can be represented as following: $B_j(z) = [A_{j1}(z) \, A_{j2}(z) \, A_{j3}(z) \ldots A_{jM}(z)]$. Here $B_j$ is the $j^{th}$ B-scan and can be described as a collection of a given number of A-scans over a transverse range (M A-scans in this case), and $A_{j1}(z)$ corresponds to the complex OCT signal for a given A-scan at a given depth (z). The complex valued OCT signal can be written as follows: $A_{jk}(z,t) = |A_{jk}(z,t)| e^{i\phi_{jk}(z,t)}$. Here $|A_{jk}(z,t)|$ is the amplitude of the complex signal and $\phi_{jk}(z,t)$ corresponds to the phase of the signal as in FIG. 2

Ideally the data will be collected while monitoring and correcting for any motion as described in US Patent Publication No. 2012/0249956 hereby incorporated by reference. Any one of a number of OCT angiography techniques (phase variance, speckle variance, Doppler, ultrahigh sensitive optical microangiography (UHS-OMAG), etc.) can be applied to the resulting complex OCT data set to resolve the motion contrast in the data. There are multiple layers of blood vessels in the retina, and various methods can be used to enhance visualization of those vessels. A common method is to enhance the contrast of the vessels by selecting regions of tissue such as anatomical layers in which the vessels are commonly found. Various methods of identifying tissue boundaries or surfaces of interest are known in the art such as intensity based local searches or global approaches on the magnitude images to extract prominent surfaces such as intreretinal layer boundaries (see for example Ishikawa, et al., "Macular Segmentation with Optical Coherence Tomography". Invest Ophthalmol Vis Sci.; 46: 2012-201, 2005). These boundaries can then be used as reference surfaces for further analysis. A reference surface could also be a simple plane through a standard or flattened OCT image volume. In cases of pathological change to the tissue, intra-retinal boundaries can become poorly defined. It is sometimes preferable to then define surfaces relative to clearly defined boundaries, such as by using mathematical combinations of identified surfaces as described in US Patent Publication No. 2013/0094720 hereby incorporated by reference. More arbitrary surfaces such as a surface generated by taking the centroids of a series of A-scans can also be envisioned by those skilled in the art. It is also possible to use the flow image or the flow image in combination with the magnitude image to find layers or surfaces. For instance, the boundary between the retina and the Choriocapillaris may be best delineated in the flow image due to the brightness of the flow signal in the choriocapillaris. The data between two surfaces, or data extending a specific range from a surface, can be defined as a layer and the layer data can be consolidated through methods such as summation or maximum intensity projection to form so-called en-face images (see for example U.S. Pat. Nos. 7,301,644 and 8,332,016 hereby incorporated by reference). The result of this summing procedure is a flat view (projection) of the volume looking along (and into) the imaging axis, and the features in this projection (en face vasculature image) capture the vascular distribution. Since the summation integrates out the depth along the axial direction, this view only captures the omnibus morphology of the vasculature, and not position in the depth direction. In general, these enhancement methods are designed to emphasize specific layers of blood vessels. These methods increase the contrast of capillary beds by eliminating signal from tissue which is unlikely to have vessels, and also have the advantage of highlighting areas without motion contrast which can correspond to tissue which is not perfused.

Figure 4:
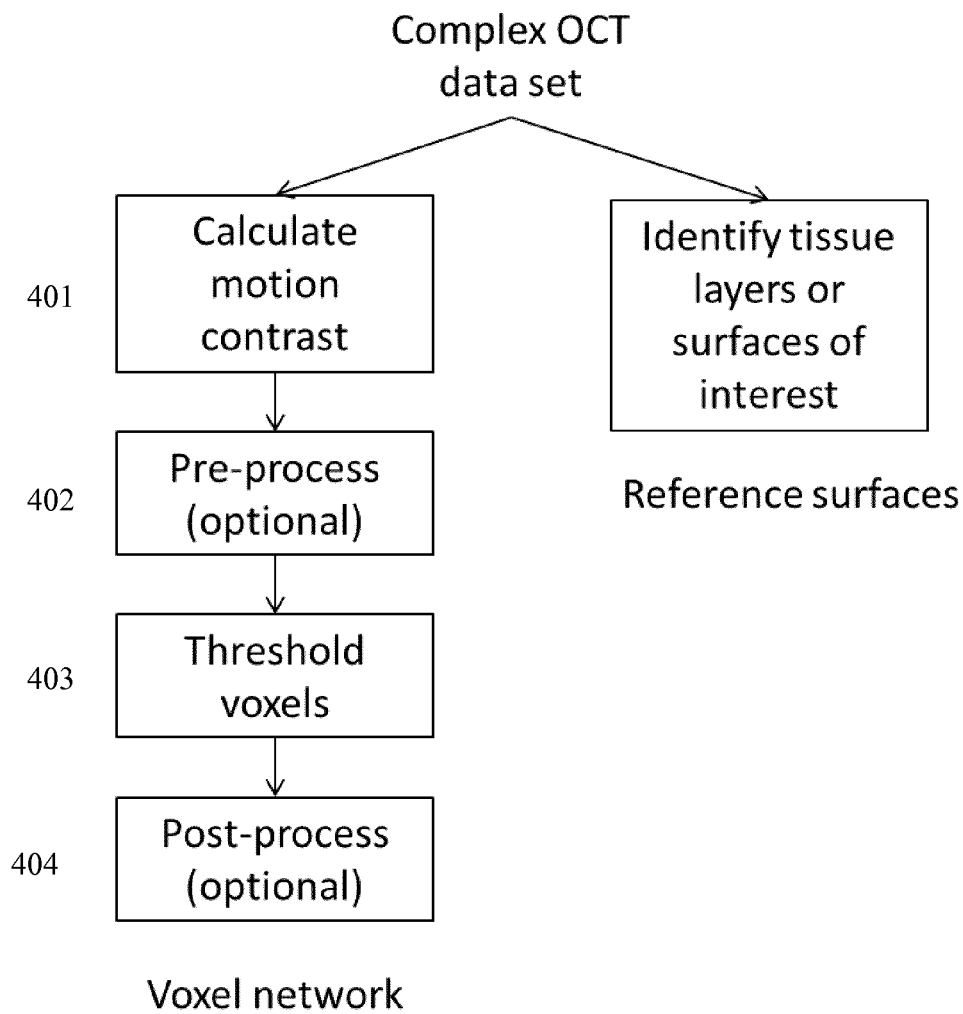
FIG. 4 is a flow-chart illustrating the initial steps involved with processing the OCT data according to the embodiments of the present application.

Here we are concerned with improving the identification of vessels that may traverse multiple retinal layers and therefore may not be easily detected or visualized by standard OCT angiography visualizations. Three different approaches to enhance visualization are considered. Initial steps related to all three approaches are illustrated in FIG. 4. The motion contrast is first calculated for each location in the volume, or voxel, of OCT data using any motion contrast technique as known in the art (step 401). Then the voxel network is determined. In one preferred embodiment, these vessels are detected by processing the volumetric data to identify voxels which demonstrate motion contrast. This detection process may include various enhancement methods known in the art of image processing such as pre-processing steps of filtering to suppress noise (step 402). Selection of the voxels can be performed by known thresholding schemes, potentially including locally varying threshold levels or hysteresis (step 403). The resulting voxel network approximates the three dimensional vascular network in the tissue. Depending on the selection of tissue to be analyzed, this network may be fully contained in the retina or fully contained in the choroid. However, in some cases it will not be constrained to either, and vessels are detected in both the retina and choroid. In situations where limitations such as poor signal to noise ratio or imperfect thresholding leave gaps in the voxel network, post-processing of the voxel network, for instance binary operations such as erosion and dilation, can improve the consistency of voxels to better approximate the true vascular network (optional step 404). One or more reference surfaces are identified as described above (step 405). These surfaces are used in subsequent steps to characterize the vessels.

Figure 5:
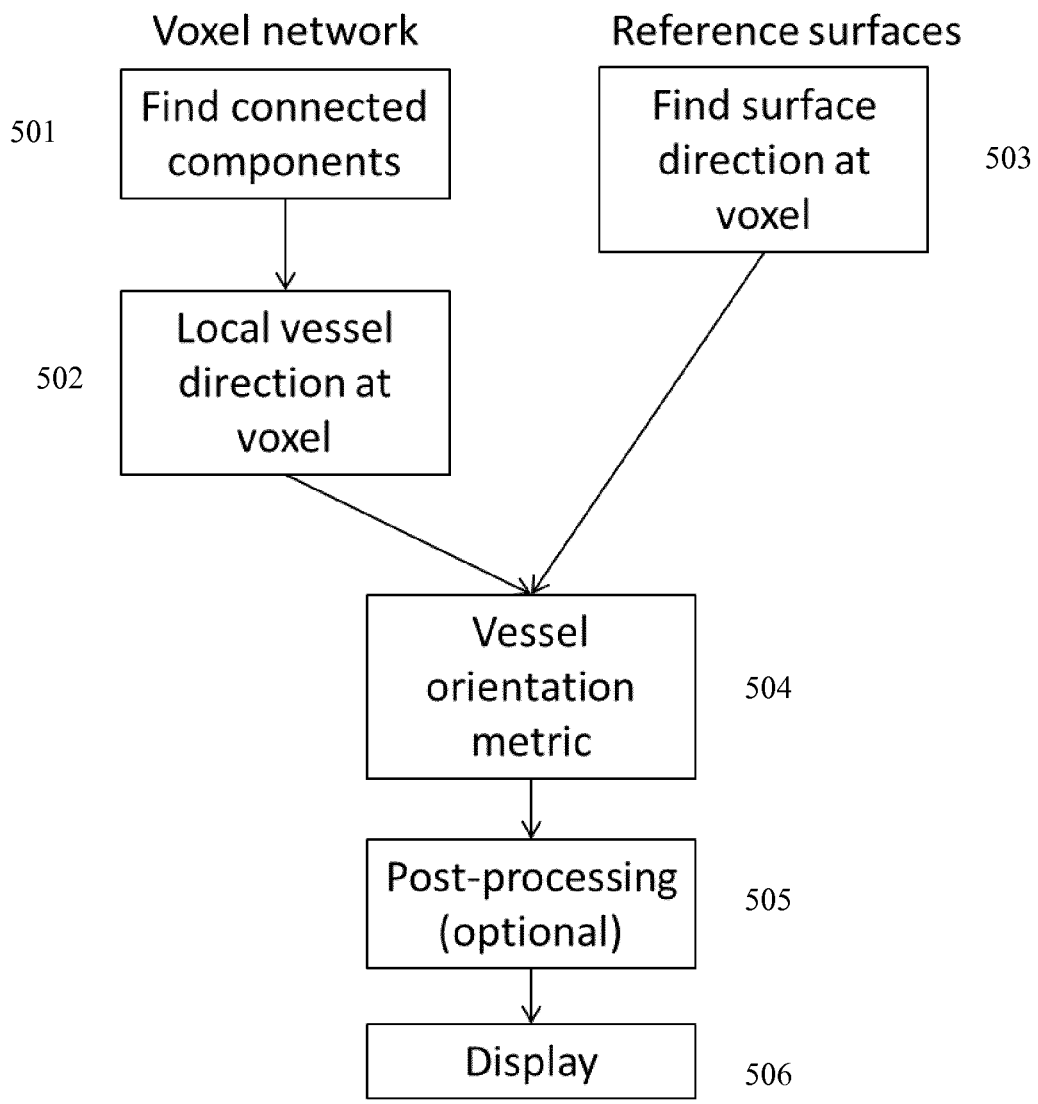
FIG. 5 is a flow-chart illustrating the steps involved with one embodiment to enhance visualization of OCT angiography data.
Figure 7:
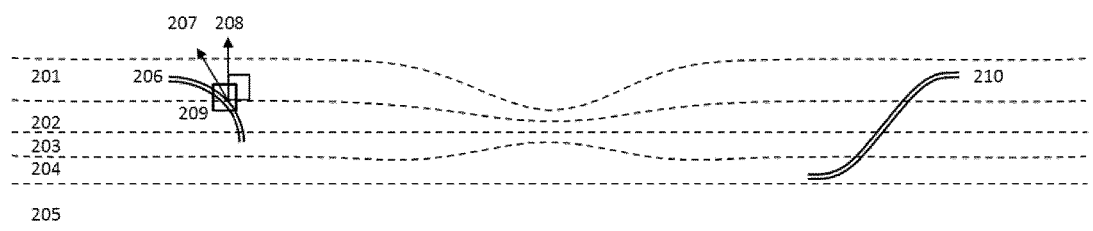
FIG. 7 is a representation of a typical B-scan of the retina indicating retinal layers and two vessels spanning multiple retinal layers.

One of the approaches of further processing of the voxel network and the reference surfaces to enhance the desired vessels is shown in FIG. 5. The collection of voxels is analyzed to identify a network of vessels. Connected component analysis is used to identify individual vessels and their connections in the network (step 501). The direction of individual vessels in the voxel network (step 502) and the reference surface directions within the network (step 503) can then be determined as illustrated in FIG. 7. FIG. 7 is a representation of a typical B-scan of the retina with retinal layers 201, 202, 203, 204 and 205 separated by intraretinal boundaries and vessels 206 and 210 each spanning or traversing multiple retinal layers. A selected voxel 209 contains a portion of vessel 206. The local direction of the vessel is calculated in three dimensional space 207. The direction can be expressed in Cartesian coordinates consistent with the original raw data, but other coordinate systems are also possible. A locally-varying coordinate system defined along natural tissue boundaries used for typical en-face images is especially useful for this application. Regardless of the coordinate system used, the resulting vessel directions are analyzed to identify vessels of interest such as those crossing intra-retinal boundaries. In one preferred embodiment, the local direction perpendicular to the retinal surfaces is defined as the vector normal to the local surface 208. For the many voxels which do not lie at the boundaries of retinal layers, a local surface can be defined as a translation of a nearby boundary or as a mathematical combination of multiple boundaries such as the ILM and RPE boundaries. Alternatively, the normal can be taken in a sampling scheme from the normal directions of one or more nearby boundaries.

The orientation of the vessel is then calculated relative to the surface normal (step 504). The relative orientation can be calculated and expressed as two or more numbers or metrics related to the three dimensional coordinate system. For instance it can be calculated from the cross-product between the vessel direction and the surface normal when the vectors are appropriately normalized. The direction relative to the local normal is most relevant to identifying those vessels crossing intra-retinal boundaries, and this can be calculated from the dot-product between the vessel direction and the normal. When the vessel direction and the normal are unit vectors, then the resulting dot product corresponds to the cosine of the angle, θ, between the vectors:

$$\cos(\theta) = v \cdot n \quad \text{(Equation 1)}$$

where v is the unit vector in the vessel direction (207) and n is unit normal vector to the local tissue surface (208).

Voxels with larger values of the metric $\cos(\theta)$ generally correspond to vessels which are crossing intra-retinal boundaries and those with smaller values generally correspond to the more common situation of vessels oriented along natural tissue boundaries or within a particular layer. The resulting data values of this metric then characterize the degree and location of vessels crossing boundaries and can be used to identify vessels of potential interest. The dot product has the advantage of being nonlinear with respect to the angle between the vectors, but other equivalent metrics can be derived from this metric, such as the angle, θ. The following teaching applies to those metrics as well.

Once vessels of interest have been identified, the data can then be displayed in several ways to enhance visualization (step 506). A preferred embodiment is to use a maximum intensity projection of the data contained between two surfaces or extending a designated distance from a particular surface resulting in a two-dimensional en face image (see for example U.S. Pat. No. 8,332,016 hereby incorporated by reference). The projection may be relative to any desired coordinate system. The A-scan direction is computationally convenient and is generally approximately perpendicular to the tissue surfaces or layers. In this representation, pixels in the projection are readily identified with the scanning coordinates of the original data. In cases where the A-scan direction is not representative of the tissue geometry, the projection may be along the local tissue boundary, such as the ILM, RPE, or other boundaries such as those used in the calculation of the metric $\cos(\theta)$. In this case, the mapping from the projection to the original data can be handled by remapping the data to a coordinate system consistent with the projection directions. In one case, the hue of the displayed vessel is encoded by the value of $\cos(\theta)$ such that values varying from zero to one map to a color look-up table from green to yellow to red. In one case, the brightness of the pixel is encoded with the intensity of the motion contrast signal.

Figure 6:
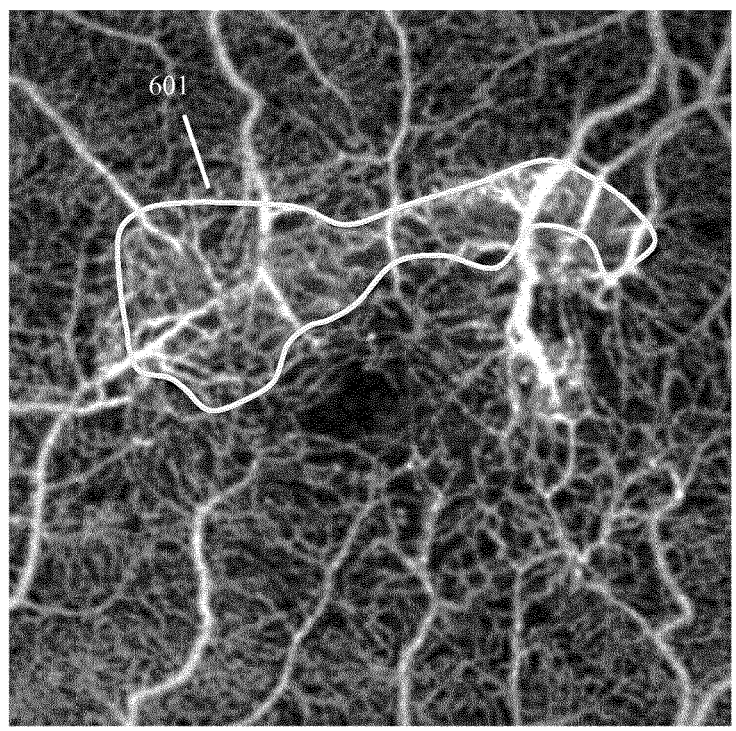
FIG. 6 shows an example of an en face OCT angiographic vasculature image highlighting a region of interest.

In another embodiment, transverse regions of the data containing vessels with larger values of the metric $\cos(\theta)$ are identified. Vasculature density or blood flow metrics can be calculated for these regions from the enface vasculature projection of various layers. Abnormally high vasculature density or blood flow metric in the vicinity of an identified region in certain specific layers (such as outer retinal layers) might be an indicator of RAP. These regions are highlighted in the display or shown at larger magnification. FIG. 6 shows an example of how regions of interest identified by the methods described herein could be highlighted in an en face projection image. In this example, a region of interest is outlined 601 to draw attention to it. B-scans illustrating the depth information for that region could also be displayed showing the vessel(s) at different heights in the different images.

The magnitude of the orientation metric can be indicated in the display through intensity mapping or color mapping. The mapping may be nonlinear to enhance the desired vessels while suppressing noise due to vessels which are roughly aligned with the tissue layers. The mapping may be usefully superimposed on other images, such as en-face images of specific layers or on representations of surfaces such as the RPE surface or thickness maps. A user interface allows selection of individual pixels in the image, and the software displaying detailed information about that scan location such as the B-scans that contain the point or magnified en-face images of the region of interest. Optional post processing such as smoothing along the vessel can be applied to the data prior to display (step 505).

Figure 8:
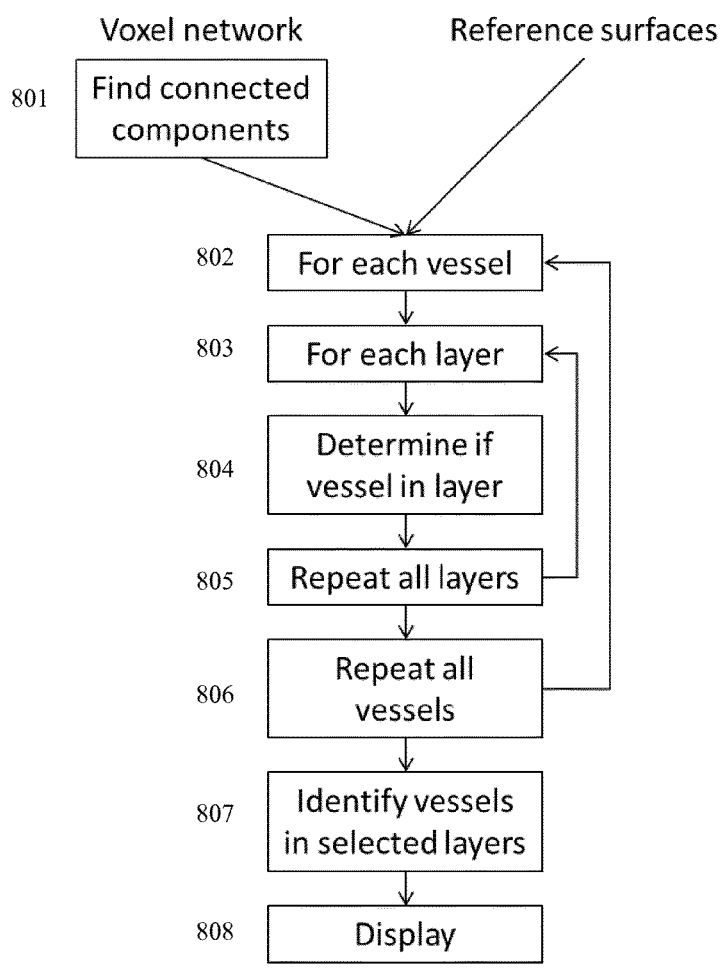
FIG. 8 is a flow chart detailing the steps involved with an embodiment to enhance vessel visualization.

In some cases of neovascularization, the orientation of the vessels may not be sufficiently different from normal vessels to detect vessels of interest based on orientation. Alternatively, the vessel network can also be analyzed to determine the path of individual vessels as shown in FIG. 8. Vessels identified by connected components analysis (step 801) can be characterized by the tissue layers in which they are found or equivalently based on the reference surfaces they cross. Because vessels typically form a circulatory loop, it is desirable to define segments of vessels of interest for the analysis. The endpoints of vessels can be defined by vessel branching or assigning a reference length, e.g. between 0.5-3 mm. The flow chart illustrates how for each vessel (step 802) in a particular layer defined by one or more reference surfaces (step 803), a determination is made if the vessel is in that layer (step 804) by comparing the vessel location to the reference layers. The process is repeated for all layers or a desired subset of layers for a single vessel (step 805) and then repeated for all vessels (step 806). Finally, the vessels in selected layers of interest can be identified (step 807) and displayed (step 808). In FIG. 7, vessel 210 is present in layers 201-204. Specific vessels to be displayed are selected based on the layer or layers in which they are found (or the surfaces which they cross). For example, vessels traversing from the nerve fiber layer to the photoreceptor layer or from the nerve fiber layer to the choroid, can be identified and displayed. Alternatively, the vessel network can be rendered with a color coding based on the number of layers in which each vessel is found or the particular surfaces it crosses.

In another embodiment, the presence of vessels of interest can be detected by creating en face images of tissue layers or regions of the data in which vessels are not normally found. The surfaces defining the layer are selected based on prior knowledge of regions which are typically non-vascularized. En-face images for these layers can be viewed in several ways, such as individual layers, combined into a single en-face image, or superimposed on other en-face images or thickness maps. For example, blood vessels are typically not found in the sub-retinal region including outer nuclear layer so this region could be segmented from the volume and a two-dimensional en face image generated from the segmented data would alert the user to any unusual vasculature in this region.

Figure 9:
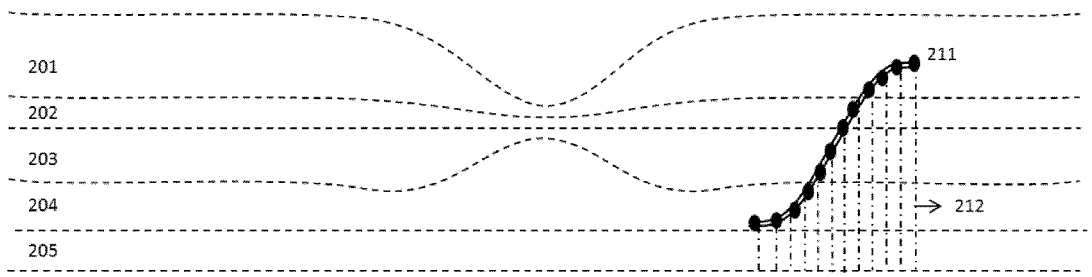
FIG. 9 is a representation of a typical B-scan showing how a vessel in the tissue could create image artifacts known as decorrelation tails.

One of the challenges in 3-D visualization of motion contrast (OCT angiography) data is the effect of de-correlation tails or shadow artifacts posterior to blood vessels. The light passing through the blood vessel passes through a region of temporally varying distribution of scatterers, which results in OCT signal variations during multiple measurements separated in time. This can sometimes cause generation of false motion contrast information under the blood vessels. The shadow artifact can cause challenges in determination of vessel orientation as illustrated in FIG. 9. In the figure, vessel 211 is present in layers 201-204. Dashed vertical lines (212) show the effect of blood vessel shadow artifacts which must be distinguished from the actual vessels of interest. Shadow artifacts appear posterior to vessels or other areas of significant temporal variation in tissue properties, along the direction of the OCT beam, and this property of the artifacts may be used to identify and suppress the artifacts. Solid circles are used in the figure to identify the actual z-location of the blood vessel.

Blood is a highly scattering medium and hence intensity information can be used to suppress the shadow artifacts. Several techniques can be implemented to minimize this artifact or minimize the impact of this artifact in determination of vessel orientation, location or path through tissue. In one approach, intensity weighted motion contrast techniques (see for example U.S. Pat. No. 8,433,393 hereby incorporated by reference) are combined with a thresholding criterion approach which could further localize the motion contrast information to within the blood vessels. In another approach, mean spatial location of the blood vessel can be ascertained by identifying either the region of maximum OCT signal contrast value, or the highest z-position (most anterior) of the thresholded OCT signal contrast value in each A-scan. The location of the blood vessel is assumed to be at this location and the signal posterior to it is ignored. The vertical extent of the vessel may be assumed to be similar to the observed lateral extent of the vessel (vessels will tend to be circular rather than extended in the vertical direction). The information from several neighboring A-scans can also be averaged to improve the localization of blood vessel spatial location, thus reducing the intensity of the artifact. Subtraction of an estimate of the flow signal from inner layers from outer signals could also compensate for decorrelation tails. Because the tails are stronger in more highly scattering areas, weighting the image to be subtracted by the intensity image (not the flow image) could improve the ability to correct for these tails in regions such as the RPE, where it is important to distinguish artifacts from real vessels. In addition, 3-D analysis of the vessel would give additional information about the orientation of the vessel despite the presence of decorrelation tails.

Although various applications and embodiments that incorporate the teachings of the present invention have been shown and described in detail herein, those skilled in the art can readily devise other varied embodiments that still incorporate these teachings. While aspects of the present application would ideally be carried out automatically within an instrument or a data processing station, one could imagine that the user could provide input to guide the analysis in some cases including but not limited to suggesting particular layers of interest, adjusting the various thresholds, or selecting particular display elements.

The following references are hereby incorporated by reference:

PATENT DOCUMENTS

U.S. Pat. No. 7,301,644
U.S. Pat. No. 8,332,016
U.S. Pat. No. 8,433,393
US Patent Publication No. 2012/0249956
US Patent Publication No. 2013/0094720
US Patent Publication No. 2013/0301008
US Patent Publication No. 2014/0028974

Non-Patent Literature

An et al. "Optical microangiography provides correlation between microstructure and microvasculature of optic nerve head in human subjects," J. Biomed. Opt. 17, 116018, 2012 Zhao et al., "Doppler standard deviation imaging for clinical monitoring of in vivo human skin blood flow," Optics Letters 25, 1358-1360, 2000

Fingler et al. "Mobility and transverse flow visualization using phase variance contrast with spectral domain optical coherence tomography" Optics Express. Vol. 15, No. 20. pp 12637-12653, 2007

Makita et al., "Optical Coherence Angiography," Optics Express, 14(17), 7821-7840, 2006

Mariampillai et al., "Optimized speckle variance OCT imaging of microvasculature," Optics Letters 35, 1257-1259, 2010
Wang et al., "Frequency domain phase-resolved optical Doppler and Doppler variance tomography" Optics Communications 242 345-350, 2004
Schmidt-Erfurth et al., "Three-Dimensional Topographic Angiography in Chorioretinal Vascular Disease," IOVS, 42 (10), 2386-2394, 2001
Avakian, et al., "Fractal analysis of region-based vascular change in the normal and non-proliferative diabetic retina," Curr. Eye Res. 24, 274-280, 2002
Schmoll et al. "Imaging of the parafoveal capillary network and its integrity analysis using fractal dimension" Biomed. Opt. Express 2, 1159-1168, 2011
Jia et al., "Quantitative OCT angiography of optic nerve head blood flow," Biomed. Opt. Express 3, 3127-3137, 2012
Jia et al. "OCT Angiography of Optic Disc Perfusion in Glaucoma" Ophthalmology, 121 (7), 1322-1332, 2014
Kim et al. "In vivo volumetric imaging of human retinal circulation with phase variance OCT," Biomedical Optics Express, 2(6), 1504-1513, 2011
Al-Diri et al. "Automated analysis of retinal vascular network connectivity," Computerized Medical Imaging and Graphics, 34, 462-470, 2010
Ganesan et al. "Development of an Image-Based Network Model of Retinal Vasculature," Annals of Biomedical Engineering 38(4) 1566-1585, 2010
Leitgeb et al. "Ultrahigh resolution Fourier domain optical coherence tomography," Optics Express 12(10) 2156, 2004
Ishikawa, et al., "Macular Segmentation with Optical Coherence Tomography". Invest Ophthalmol Vis Sci.; 46: 2012-201, 2005
Hillman et al. "Holoscopy—holographic optical coherence tomography" Optics Letters, 36(13), 2390-2392, 2011
Kim, M.-K, "Tomographic three-dimensional imaging of a biological specimen using wavelength-scanning digital interference holography" Optics Express, 7(9), 305-310, 2000
Ralston et al., "Interferometric synthetic aperture microscopy" Nature Physics, 3(2), 129-134, 2007
Hillman et al. "Holoscopy-holographic optical coherence tomography" Optics Letters, 36(13), 2390-2392, 2011
Kim, M.-K, "Tomographic three-dimensional imaging of a biological specimen using wavelength-scanning digital interference holography" Optics Express, 7(9), 305-310, 2000
Ralston et al., "Interferometric synthetic aperture microscopy" Nature Physics, 3(2), 129-134, 2007
Thorell M R et al. "Swept-Source OCT Anggiography of Macular Telangiectasia Type 2" Ophthalmic Surg Lasers Imaging Retina 45: 369-380, 2014

The invention claimed is:

1. A system for identifying potential regions of pathology in image data of an eye of a patient comprising: an optical coherence tomography (OCT) system for collecting image data of an eye of a patient, said OCT system including a light source, a sample arm, a reference arm, and a detection arm, said system further comprising: optics for directing the light source onto the eye of a patient; a light detector coupled to the detection arm for generating output signals in response to light collected from the sample arm and the reference arm; and a computer processor for receiving the output signals generated by the light detector, said processor operating to acquire at least two output signals from approximately the same location on the eye at two different times, generating complex OCT signals from the output signals, said output signals being described by an intensity and phase, said processor applying a motion contrast algorithm to the complex OCT signals to resolve the motion contrast and identifying one or more vessels in the eye using the motion contrast information, said processor identifying one or more reference surfaces relative to one or more tissue boundaries within the OCT data, and determining an angular orientation measure of the one or more vessels relative to a local surface normal of said one or more reference surfaces, and identifying vessels whose determined angular orientation measure is within a predefined range as vessels of interest, the vicinity of which defines said potential regions of pathology.

2. A system as recited in claim 1, further comprising a display for displaying the vessels of interest.

3. A system as recited in claim 2 wherein the vessels of interest are displayed on the display in a color coded en face image.

4. A system as recited in claim 1, in which the vessels of interest are vessels that cross the one or more reference surfaces.

5. A system as recited in claim 1, in which the motion contrast algorithm uses only one of the phase or intensity information from the complex OCT signals to resolve the motion contrast.

6. A system as recited in claim 1 wherein the determined angular orientation measure or a visual representation of the angular orientation measure is displayed on the display.

7. A system as recited in claim 1 wherein the processor reduces the impact of decorrelation tails or shadow artifacts on the vessels prior to determining the angular orientation of the one or more vessels.

8. A system as recited in claim 1, wherein the processor further identifies vessels of interest based on whether the vessels cross one or more of the reference surfaces.

9. A system as recited in claim 1, further comprising:
a user interface to select a layer of OCT data; and
a display for displaying an en face image of the user-selected layer of OCT data;
wherein identified potential regions of pathology within the user-selected layer of OCT data are highlighted in the displayed en face image.

10. A system as recited in claim 9, wherein the highlighting of potential regions of pathology is weighted in accordance with the determined angular orientation measure of the potential regions of pathology.

11. A system as recited in claim 1, further comprising: a user interface to select a layer of OCT data; and a display for displaying an en face image of the user-selected layer of OCT data; wherein: the processor identifies the one or more ophthalmic layers that contains a capillary bed within the user-selected layer of OCT data; the one or more reference surfaces are identified relative to one or more tissue boundaries of the ophthalmic layer that contains a capillary bed; identified potential regions of pathology within the user-selected layer of OCT data are highlighted in the displayed en face image.

12. The system of claim 1, wherein the one or more reference surfaces are identified relative to one or more ophthalmic layers within the OCT data that contain a vascular bed.

13. The system of claim 1, wherein the one or more tissue boundaries within the OCT data are identified by use of a flow image.

* * * * *

UNITED STATES PATENT AND TRADEMARK OFFICE
CERTIFICATE OF CORRECTION

PATENT NO. : 10,398,302 B2
APPLICATION NO. : 15/303819
DATED : September 3, 2019
INVENTOR(S) : Scott A. Meyer et al.

It is certified that error appears in the above-identified patent and that said Letters Patent is hereby corrected as shown below:

On the Title Page

In item (54), in Column 1, in "Title", Line 3, delete "TOMOGRAOGPHY" and insert -- TOMOGRAPHY --, therefor.

On page 3, in Column 1, under "Other Publications", Line 26, delete "7," and insert -- Vol. 7, --, therefor.

In the Specification

In Column 1, Line 3, delete "TOMOGRAOGPHY" and insert -- TOMOGRAPHY --, therefor.

In Column 5, Line 22, delete "2007)" and insert -- 2007). --, therefor.

In Column 5, Line 67, delete "FIG. 2" and insert -- FIG. 2. --, therefor.

In Column 6, Line 17, delete "intreretinal" and insert -- intra-retinal --, therefor.

In Column 11, Line 52, delete "Anggiography" and insert -- Angiography --, therefor.

Signed and Sealed this
Twenty-second Day of September, 2020

Andrei Iancu
*Director of the United States Patent and Trademark Office*